(12) United States Patent
Kessler

(10) Patent No.: US 8,277,475 B2
(45) Date of Patent: Oct. 2, 2012

(54) LAPAROSCOPIC SCISSORS

(75) Inventor: Steven C. Kessler, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 375 days.

(21) Appl. No.: 12/463,973

(22) Filed: May 11, 2009

(65) Prior Publication Data
US 2009/0281561 A1    Nov. 12, 2009

Related U.S. Application Data

(60) Provisional application No. 61/052,046, filed on May 9, 2008.

(51) Int. Cl.
A61B 17/3201    (2006.01)
(52) U.S. Cl. ............................................ 606/174
(58) Field of Classification Search .......... 606/167, 606/169, 170, 174; 30/194, 199–204, 254, 30/257
See application file for complete search history.

(56) References Cited

U.S. PATENT DOCUMENTS

| | | | |
|---|---|---|---|
| 2,790,437 A | 4/1957 | Moore | |
| 4,569,131 A | 2/1986 | Falk et al. | |
| 5,147,357 A | 9/1992 | Rose et al. | |
| 5,147,373 A | 9/1992 | Ferzli | |
| 5,174,300 A | 12/1992 | Bales et al. | |
| 5,192,298 A | 3/1993 | Smith et al. | |
| 5,290,308 A | 3/1994 | Knight et al. | |
| 5,293,878 A | 3/1994 | Bales et al. | |
| 5,304,203 A | 4/1994 | El-Mallawany et al. | |
| 5,308,358 A | 5/1994 | Bond et al. | |
| 5,312,434 A | 5/1994 | Crainich | |
| 5,331,971 A | 7/1994 | Bales et al. | |
| 5,342,381 A | 8/1994 | Tidemand | |
| 5,342,390 A | 8/1994 | Slater et al. | |
| 5,352,222 A | 10/1994 | Rydell | |
| 5,358,508 A | 10/1994 | Cobb | |
| 5,368,606 A | 11/1994 | Marlow et al. | |
| 5,383,888 A | 1/1995 | Zvenyatsky et al. | |
| 5,392,789 A | 2/1995 | Slater et al. | |
| 5,423,842 A * | 6/1995 | Michelson | 606/167 |
| 5,469,626 A * | 11/1995 | Vogel et al. | 30/266 |
| 5,478,347 A | 12/1995 | Aranyi | |
| 5,486,189 A | 1/1996 | Mudry et al. | |
| 5,496,347 A | 3/1996 | Hashiguchi et al. | |
| 5,499,992 A | 3/1996 | Meade et al. | |
| 5,522,830 A | 6/1996 | Aranyi | |
| 5,569,243 A | 10/1996 | Kortenbach et al. | |
| 5,571,137 A | 11/1996 | Marlow et al. | |
| 5,578,052 A | 11/1996 | Koros et al. | |
| 5,741,285 A | 4/1998 | McBrayer et al. | |
| 5,746,759 A | 5/1998 | Meade et al. | |
| 5,769,841 A | 6/1998 | Odell et al. | |
| 5,782,748 A | 7/1998 | Palmer et al. | |

(Continued)

*Primary Examiner* — Elizabeth Houston
*Assistant Examiner* — Anh Dang
(74) *Attorney, Agent, or Firm* — John F. Heal

(57) ABSTRACT

A laparoscopic scissor instrument can include a scissor assembly pivotally coupled to an elongate shaft. The scissor assembly can be formed of scissor blades having pivot posts thereon. The pivot posts can engage apertures on the elongate shaft, thus eliminating the need for a through-pinned pivot connection of the scissor blades. The scissor blades can also include actuation posts thereon. An actuation mechanism can include a slot to engage the actuation posts and open or close the blades of the scissor assembly. The scissor assemblies described herein can have a relatively low operational height such that they do not extend beyond a diameter of the elongate shaft during opening and closing of the scissor assembly.

10 Claims, 8 Drawing Sheets

U.S. PATENT DOCUMENTS

| | | |
|---|---|---|
| 5,782,834 A | 7/1998 | Lucey et al. |
| 5,782,859 A | 7/1998 | Nicholas et al. |
| 5,810,879 A | 9/1998 | de Guillebon |
| 5,827,323 A | 10/1998 | Klieman et al. |
| 5,849,022 A | 12/1998 | Sakahita et al. |
| 5,868,785 A | 2/1999 | Tal et al. |
| 5,928,255 A * | 7/1999 | Meade et al. ............ 606/170 |
| 5,947,996 A | 9/1999 | Logenman |
| 5,984,941 A | 11/1999 | Wilson et al. |
| 6,015,426 A | 1/2000 | Griffiths |
| RE36,795 E | 7/2000 | Rydell |
| 6,086,606 A | 7/2000 | Knodel et al. |
| 6,168,605 B1 * | 1/2001 | Measamer et al. ............ 606/174 |
| 6,193,737 B1 | 2/2001 | Ouchi |
| 6,371,956 B1 | 4/2002 | Wilson et al. |
| 6,595,984 B1 | 7/2003 | DeGuillebon |
| 7,063,697 B2 | 6/2006 | Slater |
| 7,118,587 B2 | 10/2006 | Dycus et al. |
| 2004/0225323 A1 | 11/2004 | Nagase et al. |
| 2005/0192598 A1 | 9/2005 | Johnson et al. |
| 2006/0161190 A1 * | 7/2006 | Gadberry et al. ............ 606/174 |
| 2006/0195084 A1 | 8/2006 | Slater |
| 2006/0235379 A1 | 10/2006 | McClurken et al. |

* cited by examiner

LAPAROSCOPIC SCISSORS

CROSS REFERENCE TO RELATED APPLICATIONS

This application claims the benefit of U.S. Provisional Patent Application Ser. No. 61/052,046, entitled "LAPAROSCOPIC SCISSORS", filed May 9, 2008, which is incorporated by reference herein in its entirety.

BACKGROUND

1. Field

This application generally relates to laparoscopic scissors and, more particularly, to laparoscopic scissors with blades having a parabolic cutting profile and to a mechanism for actuating the blades of the scissors.

2. Discussion of the Relevant Art

Laparoscopic surgical instruments or devices that use actuatable blades, such as laparoscopic scissors are typically activated by some mechanical means. In some cases, the surgical instruments or devices use an actuation rod to translate motion from a handle at one end to a blade at the opposite end of the device. Common to laparoscopic scissors is an actuation rod that includes a pin that works in conjunction with a slot in the blades. Moving the actuation rod cams the pin in the slot, which opens and closes the scissor blades.

In previous arrangements, the blades typically have slots proximal to a pivot location and, because of this configuration, the proximal portions, or back ends, of the blades are typically relatively large. Thus, with prior laparoscopic scissors, when the blades are in their open position, the proximal portions of the blades extend out beyond the outside diameter of the scissors shaft and look like "wings." This high-profile extension may be a problem for the user and, in particular, the patient as the extended "wings" can catch on or interfere with tissue or other devices during use.

When used on scissors, these wings can be covered by a plastic shrink tubing to insulate all the metal components during electro-surgical cautery. However, when the blades are open, the wings can stretch and deform the shrink tubing. This deformation can be problematic in that when the scissors are withdrawn from a trocar, the deformed tubing may not relax and it may catch on the end of the cannula, thereby pulling the trocar out of the patient.

SUMMARY

In general, a laparoscopic scissor instrument is provided having various aspects addressed to overcome the shortcomings in prior scissor instruments discussed above and provide certain other advantages. In some embodiments, the laparoscopic scissor instrument can include a scissor assembly with curved or parabolic cutting blades. In one aspect, a laparoscopic scissor comprises an actuation mechanism and an elongate shaft. The elongate shaft comprises an outer tube and the actuation mechanism comprises an actuation shaft movable within the outer tube. The elongate shaft can be connected to a manipulator, such as a handle assembly, and can have a scissor assembly, such as one including a first scissor blade and a second scissor blade extending from the elongate shaft. In some embodiments, the first scissor blade has a first parabolic cutting edge and the second scissor blade has a second parabolic cutting edge.

In some embodiments, a laparoscopic scissor instrument is provided comprising a handle assembly, an elongate shaft, a scissor assembly, and an actuation mechanism. The elongate shaft has a proximal end coupled to the handle assembly and a distal end. The scissor assembly is positioned at the distal end of the elongate shaft. The scissor assembly comprises a first scissor blade and a second scissor blade. The first scissor blade comprises a distal cutting portion, and a proximal actuation portion. The actuation portion comprises a pivot and an actuation protrusion. The second scissor blade comprises a distal cutting portion and a proximal actuation portion. The proximal actuation portion comprises a pivot and an actuation protrusion. The actuation mechanism extends through at least a portion of the elongate shaft and is slidable within the elongate shaft. The actuation mechanism operatively couples the handle assembly to the scissor assembly. The actuation mechanism comprises an actuation shaft and a scissor actuator. The actuation shaft has a proximal end and a distal end. The scissor actuator is at the distal end of the actuation shaft. The scissor actuator engages the actuation protrusion of the first scissor blade and the actuation protrusion of the second scissor blade.

In other embodiments, a laparoscopic scissor instrument is provided comprising an elongate tube, an actuator, and a scissor assembly. The elongate tube has a proximal end and a distal end. The actuator is axially slidable in the elongate tube. The scissor assembly is positioned at the distal end of the elongate tube. The scissor assembly comprises a first scissor blade and a second scissor blade. The first scissor blade has an interface surface and an opposed surface opposite the interface surface. The first scissor blade has a cutting portion and an actuation portion. The first scissor blade comprises a pivot protrusion and an actuation protrusion. The pivot protrusion extends outwardly from the opposed surface of the actuation portion. The pivot protrusion is pivotally coupled to the elongate tube. The actuation protrusion extends outwardly from the interface surface of the actuation portion. The actuation protrusion is operatively coupled to the actuator. The second scissor blade has an interface surface facing the interface surface of the first scissor blade and an opposed surface opposite the interface surface.

In other embodiments, a laparoscopic scissor instrument comprises a handle assembly, an elongate shaft, and a scissor assembly. The elongate shaft has a proximal end coupled to the handle assembly and a distal end. The scissor assembly is positioned at the distal end of the elongate shaft. The scissor assembly is actuatable between an open position and a closed position. The scissor assembly comprises a first scissor blade and a second scissor blade. The first scissor blade comprises a distal cutting portion and a proximal actuation portion. The distal cutting portion has a curved profile following a generally polynomial curve. The second scissor blade comprises a distal cutting portion and a proximal actuation portion. The distal cutting portion has a curved profile following a generally polynomial curve. The first scissor blade and the second scissor blade are positioned such that the curved profiles of the first scissor blade and the second scissor blade create a substantially continuous bias force between the first scissor blade and the second scissor blade as the scissor assembly is actuated between the open position and the closed position.

Many of the attendant features of the present invention will be more readily appreciated as the same becomes better understood by reference to the foregoing and following description when considered in connection with the accompanying drawings.

DETAILED DESCRIPTION

Figure 1:
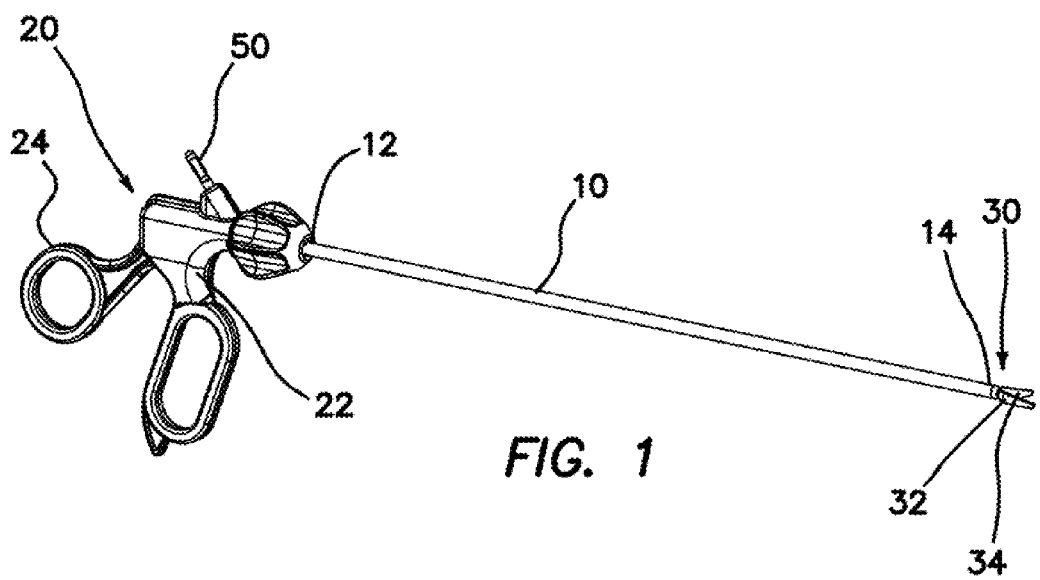
FIG. 1 is a perspective view of an embodiment of laparoscopic scissors.

With reference to FIG. 1, a laparoscopic scissors is provided having an elongate shaft 10 with a proximal end 12 connected to a manipulator, such as a handle assembly 20. Extending from a distal end 14 of the elongate shaft 10 is a scissor assembly 30, which, in some embodiments includes a pair of scissor blades pivotally movable with respect to one another. In some embodiments, the elongate shaft 10 can be sized to fit through an access port, such as a trocar cannula, that extends into an insufflated abdominal cavity for use in a laparoscopic surgical procedure. In other embodiments, the elongate shaft 10 can be sized for use in other surgical environments. In the illustrated embodiment, the elongate shaft 10 comprises an elongate generally cylindrical outer tube, although in other embodiments, the elongate shaft 10 can have other geometries such as square tubes or tubes having eccentric or oval cross-sectional profiles.

Figure 5A:
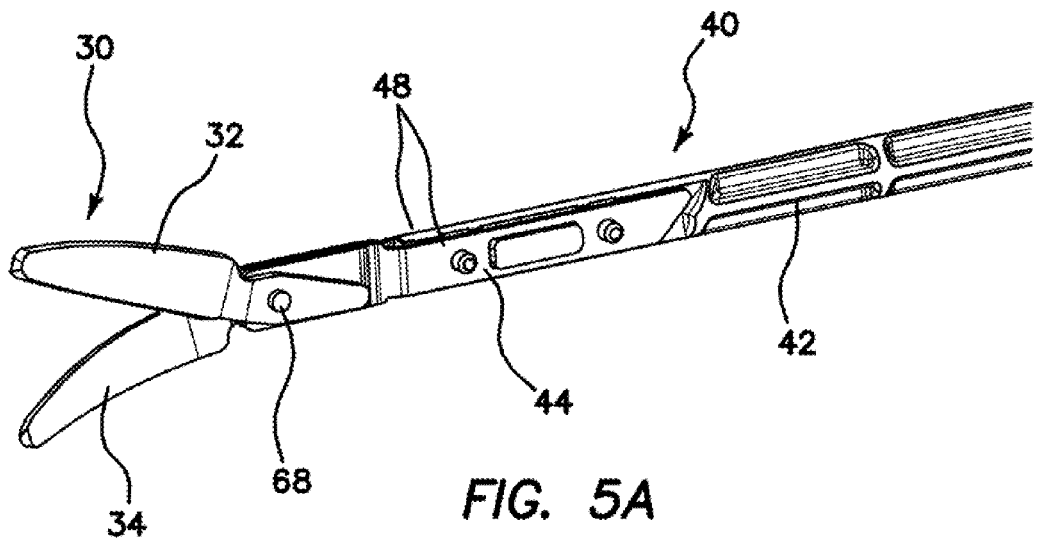
FIG. 5A is a perspective view of a scissor assembly and actuation mechanism of the laparoscopic scissors of FIG. 1.
Figure 5B:
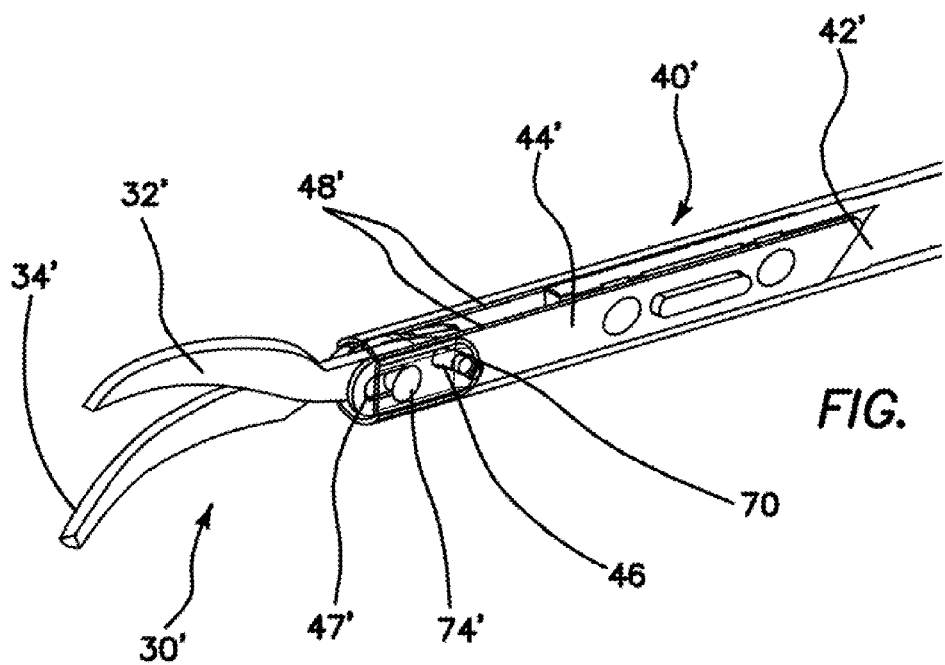
FIG. 5B is a perspective view of a scissor assembly and actuation mechanism of another embodiment of laparoscopic scissors.

An actuation mechanism 40 (FIGS. 5A, 5B, 8A, 8B) can extend through at least a portion of the elongate shaft 10 and can operatively couple the handle assembly 20 (FIGS. 8A, 8B) to the scissor assembly 30 (FIGS. 5A, 5B). A proximal end of the actuation mechanism 40 is coupled to the handle assembly 20 (FIGS. 8A, 8B), and a distal end of the actuation mechanism 40 is coupled to the scissor assembly 30 (FIGS. 5A, 5B).

The elongate shaft 10 in some embodiments is formed of a metallic material and portions of the actuation mechanism extending through the tube in some embodiments are formed of a plastic material. It is contemplated that in other embodiments, other materials may be used. Where the elongate shaft 10 is made of a metallic material, the elongate shaft 10 can be covered with an electrically insulating material or sheath, such as a plastic material, which in one aspect may be a shrink tubing material.

With reference to FIG. 1, the handle assembly 20 can comprise a stationary handle 22 and a movable handle 24. In the illustrated embodiment, through manipulation of the handle assembly 20 (e.g., moving the movable handle 24 in relation to the stationary handle 22), the actuation mechanism 40 can be longitudinally slid within the elongate shaft 10 to move the scissor assembly 30 between an open and closed configuration (FIGS. 5, 8). While the laparoscopic scissors is illustrated as having a handle assembly with a stationary handle and a movable handle, in other embodiments, it is contemplated that other handle assemblies can be used with the laparoscopic scissors described herein, such as, for example, a handle assembly having a slidable plunger, or a handle assembly having two movable handles.

In some embodiments, the laparoscopic scissor instrument can be configured to perform electrocautery. In the illustrated embodiments, the handle assembly 20 further includes an electrical connecting post 50 (FIGS. 1 and 11) to provide for cauterization of tissue during a procedure. The electrical connecting post 50 can be attached to the handle assembly 20 so as to extend at transversely to or generally perpendicular to an outer surface of the handle assembly 20 and can include an electrical conductor such as a spring or wire extending into the handle assembly 20. The electrical conductor can extend from the connecting post 50 into contact with the elongate shaft 10 to provide electrical contact to the scissor assembly 30.

With reference to FIG. 1, the scissor assembly 30 comprises a first scissor blade 32 and a second scissor blade 34. The scissor assembly 30 can be actuated between an open state and a closed state to cut items such as body tissue positioned between the scissor blades 32, 34. The first scissor blade 32 is spaced from the second scissor blade 34 when the scissor assembly is in a normal or open state. Conversely, the first scissor blade 32 is proximate the second scissor blade 34 when the scissor assembly 30 is in an actuated or closed state. The first scissor blade 32 may be considered, although not limited to, an outside or outer blade in relation to the opposing, second scissor blade 34 that may be considered, although not limited to, an inside or inner blade.

Figure 2:
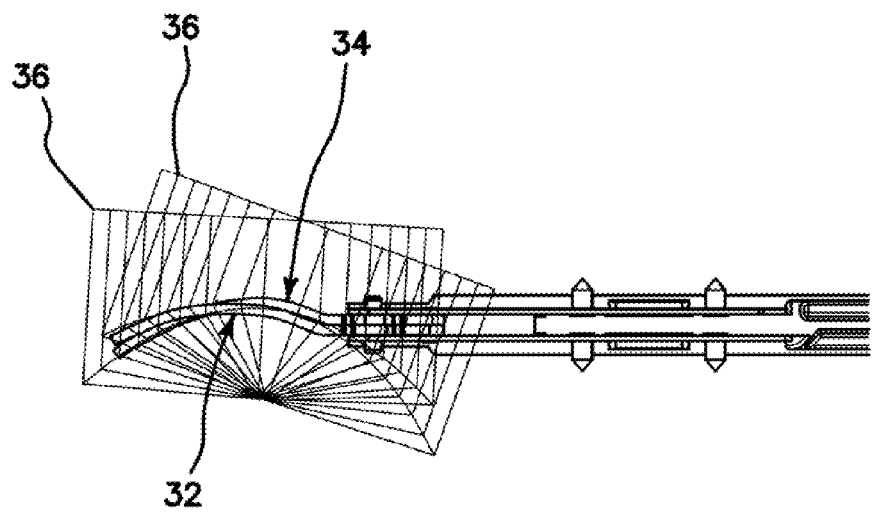
FIG. 2 is a side view of a scissor assembly of a laparoscopic scissors instrument.

With reference to FIG. 2, in some embodiments, each of the first and second scissor blades 32, 34 has a profile 36 following a curve defined by a polynomial, such as a parabola. Desirably, the relationship between the curves of the first and second blades creates continuous bias force between the blades as the scissor assembly 30 is opened and closed.

Figure 3A:
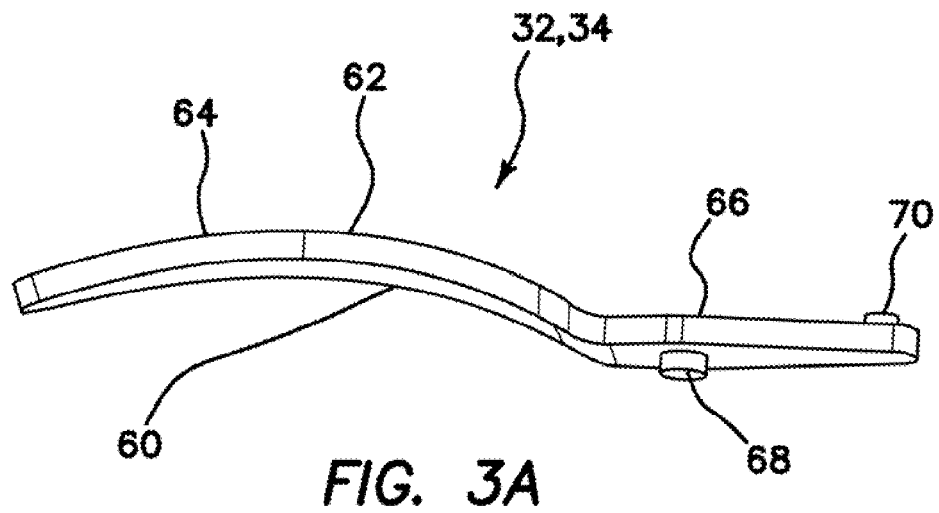
FIG. 3A is a top view of a laparoscopic scissor blade of the scissors of FIG. 1.

Referring now to FIG. 3A, one embodiment of scissor blade 32, 34 for use in embodiments of laparoscopic scissor instrument is illustrated. A single scissor blade 32, 34 is illustrated as it is contemplated that substantially identical scissor blades or manufacturing blanks for scissor blades 32, 34 can be interchangeable in some embodiments of laparoscopic scissor instrument, thus reducing manufacturing and inventory costs. However, it is contemplated that in some embodiments, the first and scissor blades can include certain variations with respect to one another. For example, in some embodiments the profile 36 discussed above can be different between the first and second blade. Also, in some embodiments, the locations and geometries of the various portions and protrusions discussed below can be different for the first and second blade. In the illustrated embodiment, the scissor blade 32, 34 has an interface surface 60, an opposing surface 62 opposite the interface surface 60, a distal, cutting portion 64, and a proximal, actuation portion 66. The scissor blade 32, 34 can further include a pivot 68 and an actuation protrusion 70 on the actuation portion 66 thereof. In the illustrated embodiment, the pivot 68 extends from the opposing surface 62 of the actuation portion 66, and the actuation protrusion 70 extends from the interface surface 60 of the actuation portion 66.

FIG. 3A illustrates an embodiment of scissor blade 32, 34 having a pivot 68 comprising a pivot protrusion. In some embodiments, the pivot protrusion can be formed on the scissor blade 32, 34. In other embodiments, the protrusion can be adhered to the scissor blade.

Desirably, the pivot protrusions extending from the opposing surfaces 62 of the scissor blades 32, 34 leave a clearance between the scissor blades 32, 34 to allow a relatively long operational stroke of the actuation mechanism as there is no pivot pin extending through (and between) both scissor blades 32, 34 in an assembled scissor assembly. Advantageously, a relatively long operational stroke can allow the actuation mechanism to be configured to deliver a relatively large amount of leverage to the scissor blades 32, 34, allowing multiple tissue types to be cut. Additionally, the relatively long operational stroke can allow the actuation mechanism and handle assembly to be configured to allow for a relatively long movement of the movable handle, thus providing enhanced fine control of the position of the scissor assembly.

In some embodiments, it can be desirable to manufacture the scissor blades 32, 34 with a process that involves relatively few low cost manufacturing steps in order to minimize cost. Accordingly, it can be desirable to form the scissor blades 32, 34 with a stamping process forming the cutting profile, which, in some embodiments, is parabolic, the pivot, and the actuation protrusion. A grinding or honing operation can then form a cutting edge 72 on the scissor blade 32, 34. In the stamping process, the pivot protrusion can be formed using a semi-perforation process. In other embodiments, the pivot protrusion and/or the actuation protrusion can be adhered or welded to the scissor blade 32, 34 after the initial forming of the scissor blade 32, 34.

Figure 3B:
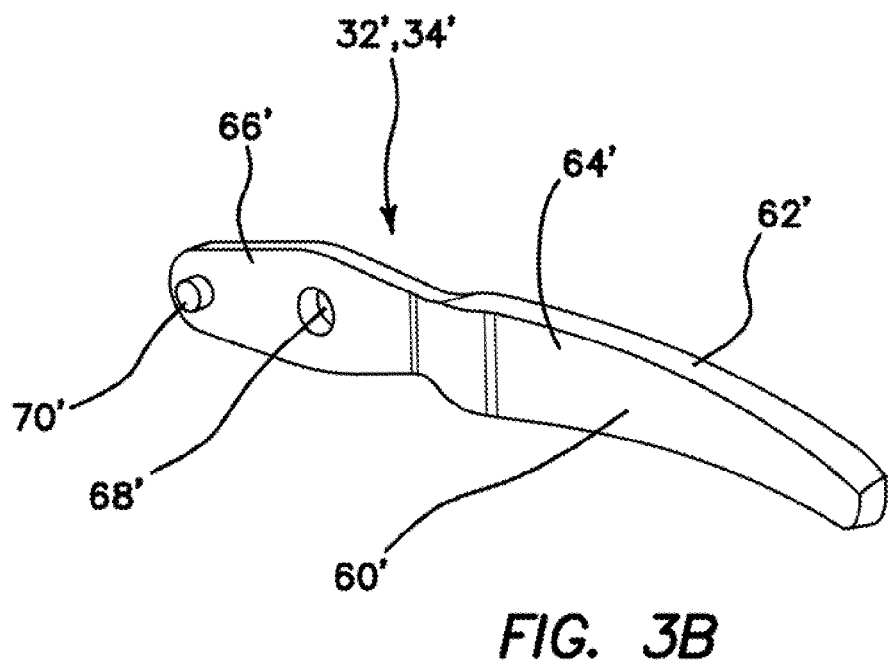
FIG. 3B is a top view of a laparoscopic scissor blade of another embodiment of laparoscopic scissors.

With reference to FIG. 3B, another embodiment of scissor blade 32', 34' for use in a laparoscopic surgical instrument is illustrated. In the illustrated embodiment, the scissor blade 32', 34' comprises an interface surface 60', an opposing surface 62', a cutting portion 64', an actuation portion 66', and an actuation protrusion 70' substantially as described above with respect to the scissor blade 32, 34 of FIG. 3A. However, in the illustrated embodiment, the scissor blade 32', 34' of FIG. 3B includes a pivot 68' comprising a pivot aperture adapted to receive a pivot pin 74' or rivet therein. As discussed above, the pivot pin 74' (FIG. 4B) can extend between the pivots 60' of each scissor blade 32', 34' and pivotably couple the scissor blades 32', 34' to one another and to the elongate shaft 10. This pivot pin 74' arrangement can shorten the operational stroke of the actuation mechanism relative to the scissor blade 32, 34 of FIG. 3A.

Figure 4A:
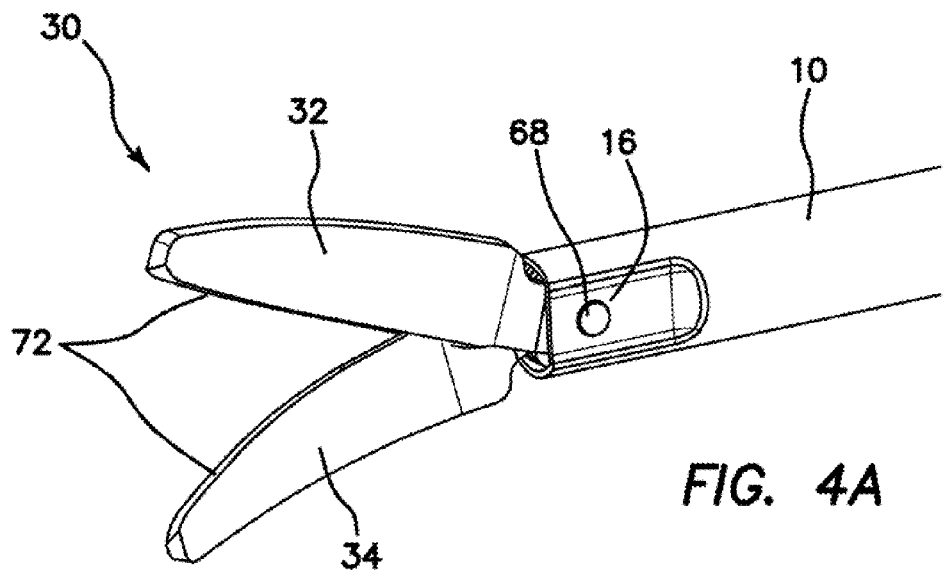
FIG. 4A is a perspective view of a scissor assembly of the laparoscopic scissors of FIG. 1.
Figure 4B:
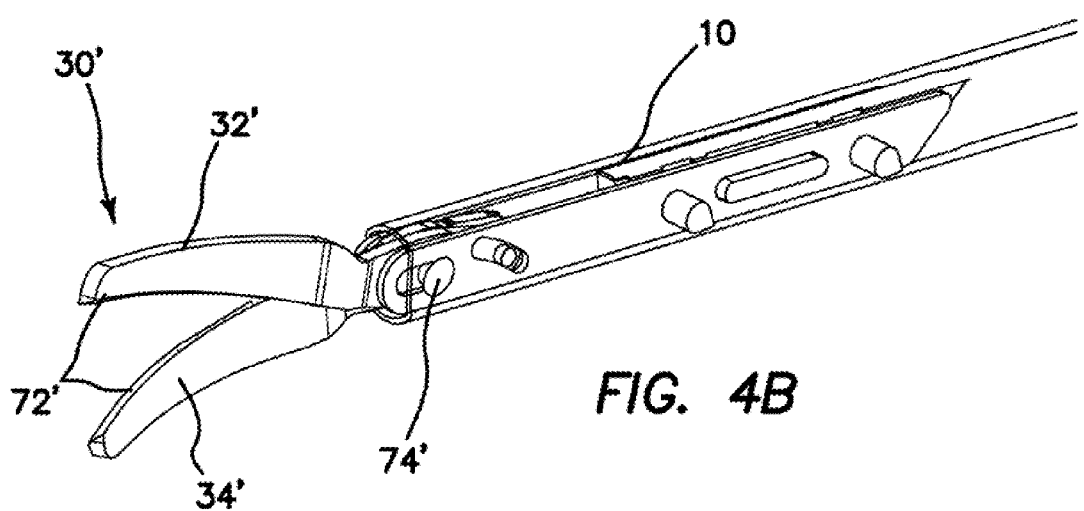
FIG. 4B is a perspective view of a scissor assembly of another embodiment of laparoscopic scissors.

With reference to the scissor blades of FIGS. 3A and 3B, each of the first and second scissor blades 32, 34, 32', 34' has a cutting edge 72, 72' that is ground at an angle (FIGS. 4A, 4B). The cutting edges 72, 72' extend from the actuation portion 66, 66' of each of the first and second scissor blades 32, 34, 32', 34' along an edge of the cutting portion 64, 64' of each of the first and second scissor blades 32, 34, 32', 34'. The cutting edge 72 of the first blade 32, 32' and cutting edge 72 of the second blade 34, 34' overlap each other and shear or cut across each other during actuation of the scissor assembly. As the actuation mechanism 40 translates through the elongate shaft 10 during a closing stroke, the point of contact or cut point progressively travels along the cutting edges 72 from a proximal portion to a distal portion of the cutting edges 72.

With reference to FIGS. 3A and 3B, the actuation portion 66, 66' of each of the first and second scissor blades 32, 34, 32', 34' can have an actuation protrusion 70, 70' that can connect the respective blade to the actuation mechanism 40. In some embodiments, the actuation protrusion 70, 70' comprises a projection, such as a post or pin. The projection can extend from the actuation portion 66, 66' of each of the first and second blades 32, 34, 32', 34' to couple the blades to camming slots in the actuation mechanism 40.

Figure 6:
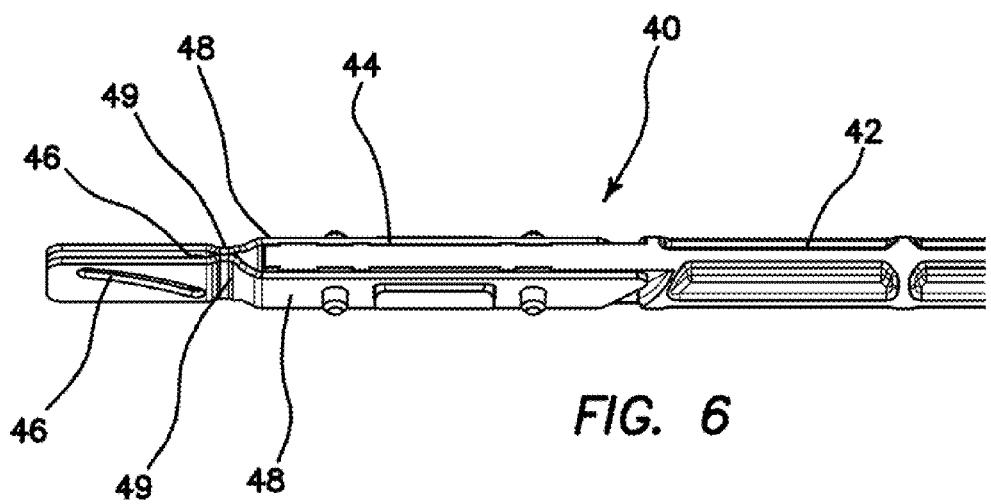
FIG. 6 is a perspective view of a distal end of an embodiment of actuation mechanism of the laparoscopic scissors of FIG. 1

With reference to FIGS. 4A, 5A, and 6, the actuation mechanism 40 can comprise an actuation shaft 42 having a proximal end and a distal end and a scissor actuator 44 at the distal end of the actuation shaft 42. In the illustrated embodiment, the scissor actuator 44 is a fork design. With the fork design, an actuation slot 46 can be formed on each fork member of the scissor actuator 44. The actuation portion 66 of the blades can be operatively coupled to the actuation mechanism 40. With a fork design scissor actuator 44, the actuation protrusion 70 of the first scissor blade 32 can be positioned in the an actuation slot 46 on one fork member of the scissor actuator 44 and the actuation protrusion 70 of the second scissor blade 34 can be positioned in the actuation slot 46 on the other fork member of the scissor actuator 44.

In some embodiments, the actuation slot 46 can extend transverse to, or in a curved arrangement relative to a longitudinal axis of the scissor actuator 44. The geometry of the actuation slot 46 can define an actuation profile for the scissor assembly. For example, a relatively steep slope of the actuation slot 46 relative to the longitudinal axis of the scissor actuator 44 can indicate an actuation profile with a relatively short stroke of the actuator and corresponding rapid opening and closing of the scissor blades 32, 34. A relatively shallow slope of the actuation slot 46 relative to the longitudinal axis of the scissor actuator 44 can indicate a relatively long actuation stroke and relatively high leverage and slow opening and closing of the scissor blades. A curved actuation slot 46 can desirably have a relatively shallow slope over portions of blade travel and a relatively steep stroke over other portions of blade travel. For example, with a curved actuation slot 46, the blades could be initially rapidly advanced towards one another for rapid initial closing of a closing actuation, then slowly advanced towards one another for a subsequent portion of a closing actuation. Thus, in a scissor device having a curved slot configuration, the scissor blades could be quickly advanced towards tissue therebetween, then more slowly advanced once the blades have contacted the tissue therebetween to provide relatively high leverage and fine control while cutting the tissue.

With continued reference to FIGS. 4A, 5A, and 6, the scissor blades 32, 34 can be pivotally coupled to the elongate shaft 10 by pivot 68 such as a pin or post on the scissor blades 32, 34. The pivot 68 on each blade can engage with a corresponding aperture 16 formed in the distal end 14 of the elongate shaft 10. Thus, the engagement of the pivots 68 of each blade 32, 34 with the elongate shaft 10 allows the blades 32, 34 to pivot about the pivot 68 when the scissor assembly 30 is actuated between the open and closed configurations. When the actuation mechanism 40 is moved in one direction, the actuation protrusions 70 of each of the blades 32, 34 will cam against their respective actuation slots 46 on the actuation mechanism 40.

In some embodiments, the actuation mechanism 40 may be a single integral component, or, in other embodiments may have multiple pieces assembled together. With continued reference to FIGS. 4A, 5A, and 6, in some embodiments, the scissor actuator 44 includes a fork design including fork members each comprising a separate flanking plate 48. In some embodiments, the flanking plates 48 can each be coupled with a distal end of the actuation shaft 42. A proximal portion of each of the flanking plates can be adapted to mate and couple with a distal portion of the actuation shaft 42, and a distal portion of each of the flanking plates 48 can be adapted to mate with and actuate one of the scissor blades 32, 34. In some embodiments, each of the flanking plates 48 is coupled to the actuation shaft 42 by heat staking. In other embodiments, each of the flanking plates can be coupled to the actuation shaft 42 by press-fit, fastener, adhesive, or another mechanical or chemical process. The flanking plates 48 can include one or more apertures, slots, recesses, grooves, or other feature to facilitate coupling of the flanking plates to the actuation shaft 42.

In some embodiments, the scissor actuator 44 of the actuation mechanism 40 can be configured to apply a biasing force to the scissor assembly 30. Advantageously, a biasing force on the scissor assembly 30 can maintain a cutting contact between cutting edges 72 of the first and second scissor blades 32, 34 throughout the range of motion of the scissor assembly 30 from the open position to the closed position. With reference to FIGS. 4A, 5A, and 6, in the illustrated embodiment, the fork design of the scissor actuator 44 can be configured such that the flanking plates 48 apply a biasing force to the scissor assembly 30. In the illustrated embodiment, each flanking plate 48 includes a bend 49 or knuckle. When the flanking plates 48 are coupled to the actuation shaft 42 to form the scissor actuator 40, the bends 49 of the flanking plates 48 bear on one another such that an outward biasing force is applied to the actuation portions 66 of the scissor blades 32, 34 (FIG. 5). This outward biasing force on the actuation portions 66 proximal of the pivot 68 tends to bias the cutting portions 64 of the scissor blades 32, 34, towards one another. Thus, the ability of the scissor assembly to cut various tissue types is enhanced.

With reference to FIGS. 4B and 5B an actuation mechanism 40' for coupling to a laparoscopic scissor instrument having pinned pivoting blades, such as those illustrated in FIG. 3B is illustrated. In the illustrated embodiments, the actuation mechanism 40' includes an actuation shaft 42' coupled to a scissor actuator 44', substantially as discussed above with respect to the embodiment of FIGS. 4A, 5A, and 6. The scissor actuator 44' includes an actuation slot 46' formed at a distal end thereof. In the illustrated embodiment, the scissor actuator 44' comprises a forked design having two flanking plates 48' each having an actuation slot 46' formed therein. However, each flanking plate 48' also includes a pivot slot 47' adapted to receive the pivot pin 74'. Accordingly, the actuation slot 46' of the scissor actuator 44' of FIGS. 4B and 5B is relatively short compared to the actuation slot 46 of the scissor actuator 44 of FIGS. 4A, 5A, and 6. Thus, a scissor instrument having pinned-pivot scissor blades (such as those illustrated in FIGS. 4B and 5B) tends to have a shorted actuation stroke than a scissor instrument having pin-less scissor blades (such as those illustrated in FIGS. 4A, 5A, and 6).

With continued reference to FIGS. 4B and 5B, with the flanking plates 48' coupled to the actuation shaft 42', the distal portions of the flanking plates 48' are spaced from each other such that the actuation portions 66' of each of the first and second scissor blades 32', 34' may be positioned between distal portions of the flanking plates 48'. This spaced arrangement of the flanking plates 48' differs from the bias-generating bends 49 of the flanking plates 48 of the scissor actuator 44 of FIGS. 4A, 5A, and 6.

With continued reference to FIGS. 4B and 5B, as noted above, the distal portion of each of the flanking plates 48' has a generally-longitudinally extending pivot slot 47' that provides clearance for the pivot pin 74' as the actuation mechanism 40' is moved distally and proximally within the elongate shaft 10. Desirably, the pivot slots 47' can be sufficiently long to provide for a full stroke length of the scissor assembly 30'.

With continued reference to FIGS. 4B and 5B each of the flanking plates 48' also has a slanted or curved actuation slot 46' into which the actuation protrusion of the respective scissor blade 32', 34' can be positioned. The actuation slots 46' extend transversely to each other to facilitate opening and closing of the scissor blades 32', 34' as the actuation mechanism 40' translates distally and proximally within the elongate shaft 10.

With continued reference to FIGS. 4B and 5B, as discussed above, the flanking plates 48' may be coupled to the actuation shaft 42' by methods such as heat staking, fasteners, and adhesive. The flanking plates 48' and the actuation shaft 42' may have mating features, such as a raised projection for mating into an aperture, to facilitate proper positioning of the flanking plates 48' in relation to the actuation shaft 42'. Similarly, the flanking plates 48' and actuation shaft 42' may have features, such as angled surfaces at the proximal end of the flanking plates that conform to a surface on the actuation shaft 42', for ensuring that each flanking plate 48' is positioned on the proper side of the actuation shaft 42' and oriented in the proper position.

Advantageously, in a laparoscopic instrument, a scissor assembly 30, 30' having pins on scissor blades 32, 34, 32', 34' to mate with a slotted actuation mechanism 40, 40' can have a reduced operational height as compared with a scissor assembly having slots formed on scissor blades driven by an actuated pin. Thus, desirably the scissor assemblies 30, 30' described herein can be configured such that their operational height is smaller than a diameter of the elongate shaft 10. Accordingly, during an open or close stroke of the scissor assembly 30, 30', substantially no portion of the scissor blades 32, 34, 32', 34' protrudes beyond the diameter of the elongate shaft 10. Accordingly, the scissor assemblies described herein advantageously have a reduced "wingspan," and thus a reduced risk of interfering with tissue or distorting an elastomeric sheath around the elongate shaft.

While various methods of manufacturing the blades of FIG. 3A are discussed above, it is appreciated that there are numerous methods and processes of manufacturing the blades that can be used in addition to or in combination with the methods discussed above. For example, in some embodiments, the blades 32, 34, 32', 34' can be formed from conventional stamping and then heat treated. In other embodiments, the blades 32, 34, 32', 34' can be formed from a blank of pre-hardened material and then EDM cut, waterjet cut, laser cut or even machined to obtain the final shape. It should be noted that the protrusions, projections or pins of the actuation portions of the blades 32, 34, 32', 34' can be formed directly onto the blades, or they can be added to the blades 32, 34, 32', 34' as a separate component.

Protrusions or pins that are made as separate components from the blades can be attached to the blades in any one or a combination of ways. For example, in various embodiments, the protrusions can be press-fitted, swaged, threaded and/or welded to the blades 32, 34, 32', 34'. To manufacture the pin as part of the blades 32, 34, 32', 34', a multitude of processes can be used. A sheet of material can be stamped or machined to include a pivot 68' hole as well as the actuation protrusion 70' pin or a pivot 68 protrusion and actuation protrusion 70. The sheet can then be heat treated and sent to a form grinder, which can grind one profile of the blade 32, 34, 32', 34'. The ground plate can then be sent to be EDM cut and the second profile can be cut out. This type of process can yield numerous components, with the actuation protrusion pin 70, 70' and pivot 68 protrusion integrally located, for relatively low cost.

There are also additional processes that can yield the entire part from a minimum number of operations. These can include, but are not limited to, metal injection molding (MIM), casting, and powder metallurgy (PM). The final blade can also then be sent to be sharpened or other post-processing.

The following is a discussion of the pin and slot design of the laparoscopic scissor instruments described herein, where there are a number of advantages which can be realized. For example, the proximal, actuation portion 66, 66' of each blade 32, 34, 32', 34' has a relatively reduced area. In this manner, very little or no part of the blades 32, 34, 32', 34' of the scissor assembly 30, 30' extend beyond the diameter of the elongate shaft 10 during actuation of the scissor assembly 30, 30'. This reduces the risk of substances catching on the blades 32, 34, 32', 34' during scissor use and likewise reduces the risk that a sheath such as shrink tubing found on scissors would be deformed during scissor use.

Figure 7:
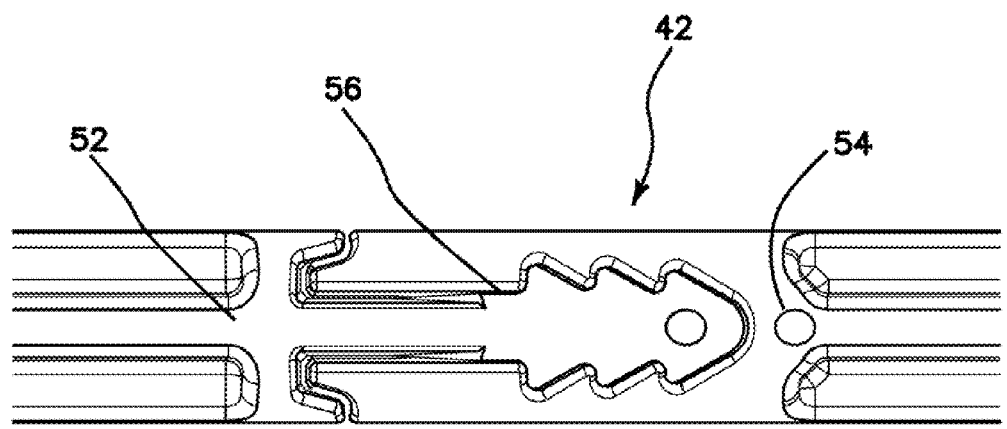
FIG. 7 is a top view of an embodiment of actuation mechanism of the laparoscopic scissors of FIG. 1.

With reference to FIG. 7, to facilitate manufacturing of the actuation mechanism 40, 40', the actuation shaft 42, 42' may be made in two or more shaft portions 52, 54. If made in separate shaft portions 52, 54, the shaft portions 52, 54 should be coupled by a connection 56 that can withstand two or more times the maximum service tension of the actuation mechanism 40, 40'. For example, if the maximum service tension is twenty-eight pounds, then the connection 56 should desirably be able to withstand tension of fifty-six pounds.

With continued reference to FIG. 7, in one embodiment, a connection 56 having a sequential barbed configuration is illustrated. The connection 56 has a shape similar to a fir tree, on a first actuation shaft portion 52 that mates to a mating female portion on a second actuation shaft portion 54. The barbs of the "fir tree" may be sequentially smaller from the base to the tip. In this configuration, the female portion may tend to open or separate when tension is applied to the actuation shaft 42, 42'. To prevent this opening, the mating ends may each include a male portion and a female portion so that the end of the male mating portion of each piece of the actuation rod is covered by the female mating portion of the adjoining piece of the actuation rod. The mating ends may also be configured to snap-fit together, such as by a slight mismatch at the parting lines of the pieces of the actuation rod. While the connection 56 is illustrated as a sequential barbed connection, it is contemplated that in other embodiments, other connection types can be used to connect portions of actuation shafts in laparoscopic scissor instruments described herein.

Figure 8A:
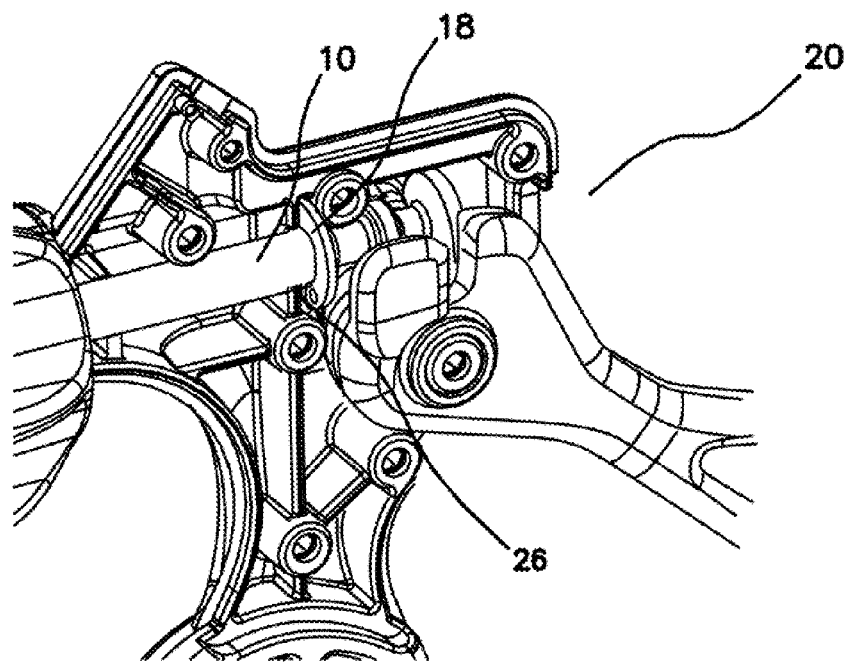
FIG. 8A is a perspective view of an interior of an embodiment of handle assembly of the laparoscopic scissors of FIG. 1.
Figure 8B:
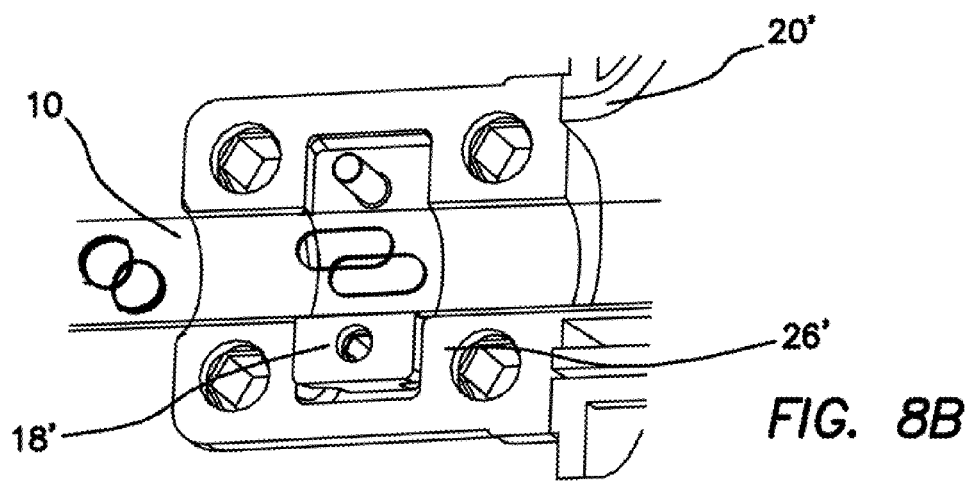
FIG. 8B is a perspective view, partially in cross-section, of an interior of a handle assembly of another embodiment of laparoscopic scissors.

With reference to FIGS. 8A and 8B, to maintain the position of the elongate shaft 10 longitudinally in relation to the handle assembly 20, a proximal portion of the elongate shaft 10 may have a retention member 18, 18' projecting radially therefrom that fits into a retention cavity 26, 26' in the handle assembly 20, 20'.

FIG. 8A illustrates one embodiment of retention member 18 comprising a retention clip. The retention clip can be secured to the elongate shaft 10 in slots formed in an outer surface of the shaft. The retention clip can maintain a longitudinal position of the elongate shaft relative to the handle assembly 20 by interfacing with a retention cavity 26 that can be formed of a first retention rib positioned proximally to the retention clip and a second retention rib positioned distally to the retention clip. This interface between retention member 18 and retention cavity 26 allows the elongate shaft 10 to be rotated relative to the handle assembly about a longitudinal axis of the elongate shaft 10, but restricts the elongate shaft 10 from being moved axially with respect to the handle assembly about the longitudinal axis.

FIG. 8B illustrates another embodiment of retention member 18' for use in some embodiments of laparoscopic scissor instrument. The retention member 18' comprises a retention collar that can be attached onto the elongate shaft 10 by one or a combination of coupling techniques, such as fasteners, adhesives, and mating protrusions and apertures. In the illustrated embodiment, the collar is made from two or more identical pieces coupled together around the tube of the shaft. The retention collar 18' can engage with a retention cavity 26' formed in the handle assembly 20' such that the elongate shaft 10 is rotatable with respect to the handle assembly 20', but axial movement of the elongate shaft 10 with respect to the handle assembly 20' is restricted.

Figure 9A:
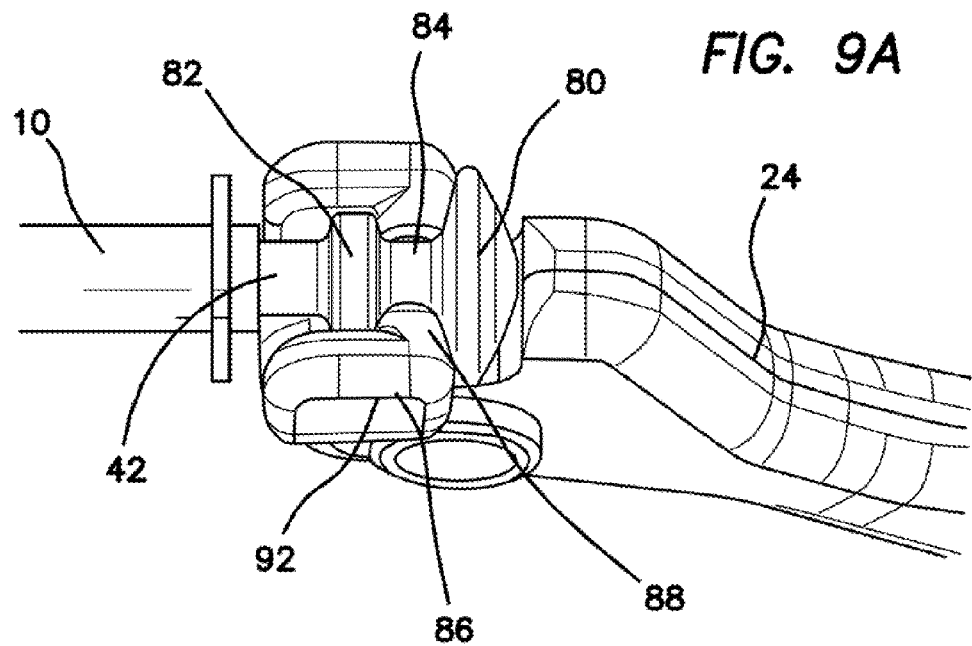
FIG. 9A is a perspective view of an embodiment of handle assembly to actuation mechanism connection of the laparoscopic scissors of FIG. 1.
Figure 9B:
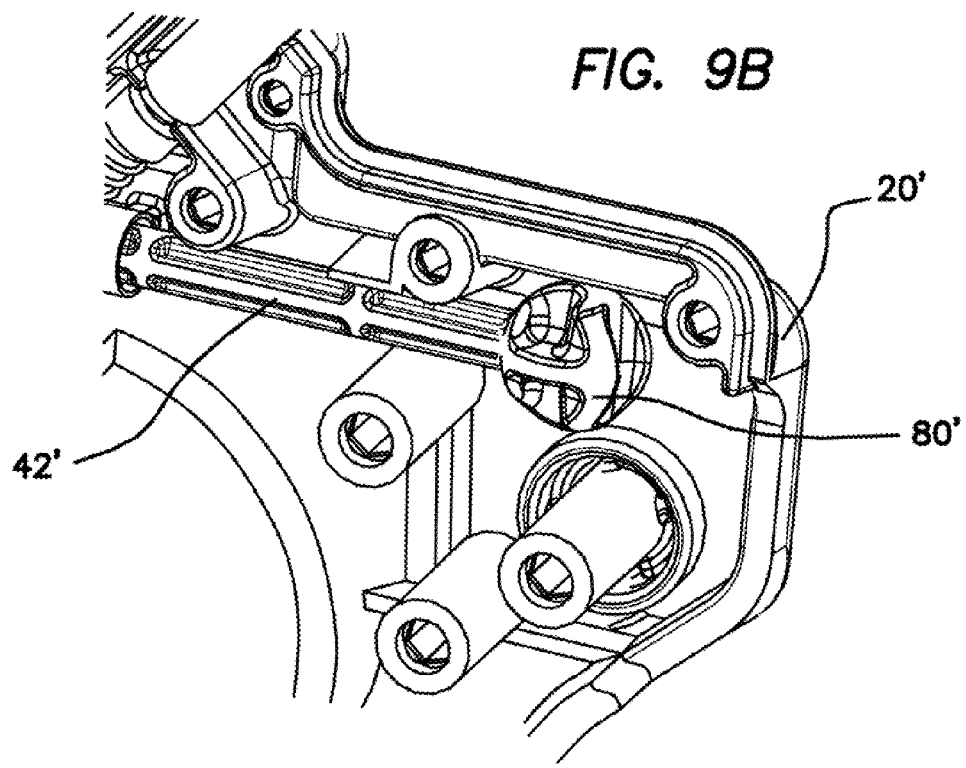
FIG. 9B is a perspective view of an embodiment of handle assembly to actuation mechanism connection of another embodiment of laparoscopic scissors.

With reference to FIGS. 9A and 9B, various embodiments for coupling the actuation mechanism 40, 40' to the movable handle 24 of the handle assembly 20 are illustrated. FIG. 9A illustrates a first embodiment in which a first actuation disc 80 and a second actuation disc 82 are formed on the proximal end of the actuation shaft 42, forming a space 84 therebetween. The actuation discs 80, 82 can be integrally formed with the actuation shaft 40 or can be joined thereto by mechanical or chemical fastening or adhesive. In the illustrated embodiment, the actuation discs 80, 82 can have different sizes such that for example, the first actuation disc 80 has a larger diameter and thickness than the second actuation disc 82. In some embodiments, it can be desirable that at least one of the actuation discs 80, 82 has a diameter large enough to interfere with a wall of the handle assembly to limit lateral movement of the actuation mechanism transverse to the longitudinal axis of the elongate shaft 10. In other embodiments, the actuation discs 80, 82 can be substantially the same size and shape, or can have other variations in size and shape than the illustrated embodiment. (For example, in some embodiments, the second actuation disc 82 can be thicker and have a larger diameter than the first actuation disc 80).

With continued reference to FIG. 9A, in the illustrated embodiment, a retention clamp 86 is formed on the movable handle 24 and engages with at least one of the discs 80, 82, and the space 84 such that movement of the movable handle axially slides the actuation shaft 42 within the elongate tube 10. The retention clamp 86 can include gripping flanges 88 adapted to engage at least one of the discs 80, 82, and the space 84 and sidewalls 92 adapted to maintain the coupling between the actuation shaft 42 and the movable handle 24. Desirably, the retention clamp 86 can be sized and configured to perform repeated scissor actuation cycles cutting various tissue types without fracturing, failing, or slipping off of the actuation discs 80, 82. In some embodiments, the retention clamp 86 can have a rounded profile to reduce stress concentrations at curved portions thereof.

Advantageously, the disc shapes are relatively simple to manufacture. Furthermore, the actuation disc assembly illustrated in FIG. 8A is relatively low profile and allows rotation of the actuation mechanism 40 with respect to the handle assembly 20 about the longitudinal axis of the elongate shaft 10.

FIG. 9B illustrates another embodiment of coupling between the actuation mechanism 40' and the movable handle 24. The coupling includes an enlarged proximal end such as an actuation ball 80' adapted to mate to a retention clamp on the movable handle. The actuation ball 80' can be integrally formed with the actuation shaft 42', or can be joined thereto by other mechanical or chemical coupling such as a fastener or adhesive coupling. Thus, the actuation ball 80' can fit into a mating groove or cavity formed in the retention clamp to provide a rotatable ball-and-socket joint.

Figure 10:
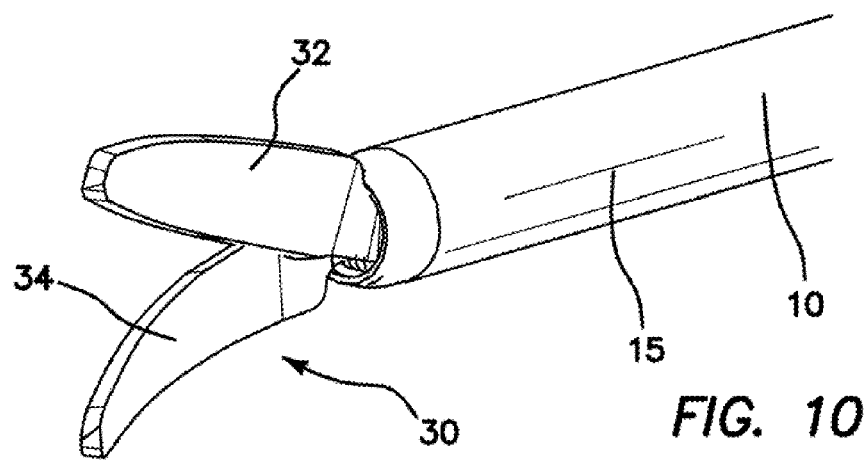
FIG. 10 is a perspective view of a distal end of the laparoscopic scissors of FIG. 1.

With reference to FIG. 10, a distal end of various embodiment of laparoscopic scissors is illustrated with a sheath 15, such as an electrically insulating shrink tube disposed about the elongate shaft 10. As shown in FIG. 10, and as further discussed above, advantageously, the scissor assembly 30 can be configured such that an operational height of the scissor assembly is smaller than a diameter of the elongate shaft 10 such that the scissor blades 32, 34 remain inside diameter of the elongate shaft, and the sheath 15 is not distorted or distended during operation of the scissors.

Figure 11:
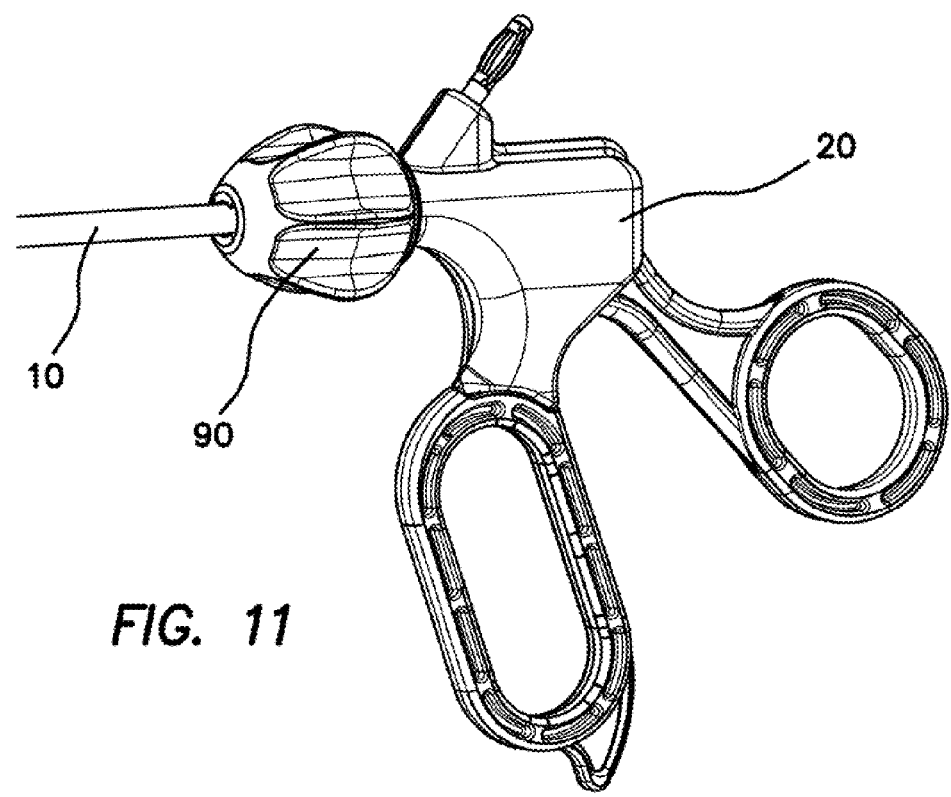
FIG. 11 is a perspective view of a proximal end of the laparoscopic scissors of FIG. 1.

With reference to FIG. 11, in some embodiments, the laparoscopic scissors can include a rotatable elongate shaft such that a user can rotate the scissor assembly 30 as desired during use. In some embodiments, the elongate shaft can have infinite 360 degree rotation relative to the handle assembly. In other embodiments, it can be desirable to have rotation stops to limit the rotation of the elongate shaft to a predetermined range. The laparoscopic scissors can include a rotational knob 90 coupled to the elongate shaft 10 allowing the elongate shaft 10 and scissor assembly 30 to rotate relative to the handle assembly 20 about the longitudinal axis of the elongate shaft 10. As discussed above, the couplings between the handle assembly and the elongate shaft 10 can be configured to allow rotation therebetween about the longitudinal axis of the elongate shaft 10.

Many alterations and modifications may be made by those having ordinary skill in the art without departing from the spirit and scope of the invention. For example, various combinations and subcombinations of certain features and aspects of the various embodiments described above can be made to form certain other embodiments of scissor within the scope of the described laparoscopic instrument. For these reasons, the above description should not be construed as limiting the devices described herein, but should be interpreted as merely exemplary of the embodiments. Accordingly, the scope of the present devices should be made in accordance with a fair reading of the claims that follow.

What is claimed is:

1. A laparoscopic scissor instrument comprising:
a handle assembly;
an elongate shaft having a proximal end coupled to the handle assembly, and a distal end;
a scissor assembly positioned at the distal end of the elongate shaft; the scissor assembly comprising:
a first scissor blade comprising:
a distal cutting portion, and
a proximal actuation portion, the actuation portion comprising a pivot and an actuation protrusion; and
a second scissor blade comprising:
a distal cutting portion, and
a proximal actuation portion comprising a pivot and an actuation protrusion; and
an actuation mechanism extending through at least a portion of the elongate shaft and slidable within the elongate shaft, the actuation mechanism operatively coupling the handle assembly to the scissor assembly, the actuation mechanism comprising:
an actuation shaft having a proximal end and a distal end; and
a scissor actuator at the distal end of the actuation shaft, the scissor actuator comprising: a first actuator plate engaging the actuation protrusion of the first scissor blade; and
a second actuator plate engaging the actuation protrusion of the second scissor blade, and
wherein the first actuator plate comprises a compression bend and the second actuator plate comprises a compression bend positioned to contact and engage the compression bend of the first actuator plate and generate a bias force between the first scissor blade and the second scissor blade.

2. The instrument of claim 1, wherein the pivot of the first scissor blade comprises a protrusion.

3. The instrument of claim 2, wherein the protrusion comprises a post.

4. The instrument of claim 1, wherein the pivot of the first scissor blade is integrally formed with the first scissor blade.

5. The instrument of claim 4, wherein the pivot of the first scissor blade is formed by a semi-perforation technique in a stamping operation.

6. The instrument of claim 5, wherein the pivot of the second scissor blade is formed by the formed by a semi-perforation technique in a stamping operation.

7. The laparoscopic scissor instrument of claim 1, wherein the distal cutting portion of the first scissor blade has a curved profile following a generally polynomial curve; and the distal cutting portion of the second scissor blade has a curved profile following a generally polynomial curve.

8. The instrument of claim 7, wherein the curved profile of the first scissor blade and the curved profile of the second scissor blade each follow a generally parabolic curve.

9. The instrument of claim 1, wherein the actuation shaft comprises a first shaft portion and a second shaft portion coupled by a shaft connector.

10. The instrument of claim 9, wherein the shaft connector comprises a sequential barbed configuration.

* * * * *